US012599738B1

(12) United States Patent
Stramiello

(10) Patent No.: US 12,599,738 B1
(45) Date of Patent: Apr. 14, 2026

(54) ORAL AND NASAL TRACHEAL INTUBATION ASSISTANCE DEVICE

(71) Applicant: Joshua Anthony Stramiello, Lakenheath (GB)

(72) Inventor: Joshua Anthony Stramiello, Lakenheath (GB)

( * ) Notice: Subject to any disclaimer, the term of this patent is extended or adjusted under 35 U.S.C. 154(b) by 0 days.

(21) Appl. No.: 19/096,793

(22) Filed: Apr. 1, 2025

(51) Int. Cl.
*A61M 16/04* (2006.01)

(52) U.S. Cl.
CPC .............................. *A61M 16/0488* (2013.01)

(58) Field of Classification Search
CPC .......... A61M 16/0488; A61M 16/0409; A61M 16/0411; A61M 16/0418; A61M 16/0497
See application file for complete search history.

(56) References Cited

U.S. PATENT DOCUMENTS

| | | | |
|---|---|---|---|
| 4,365,625 A | 12/1982 | Rind | |
| 4,546,762 A * | 10/1985 | Upsher | A61B 1/267 600/199 |
| 5,163,941 A * | 11/1992 | Garth | A61M 16/0461 24/518 |
| 5,174,283 A | 12/1992 | Parker | |
| 5,203,320 A * | 4/1993 | Augustine | A61M 16/0488 128/207.14 |
| 5,282,816 A | 2/1994 | Miller | |
| 5,743,254 A | 4/1998 | Parker | |
| 6,053,166 A * | 4/2000 | Gomez | A61M 16/0493 128/207.14 |

| | | | |
|---|---|---|---|
| 6,655,377 B2 | 12/2003 | Pacey | |
| 6,672,305 B2 * | 1/2004 | Parker | A61M 16/0495 128/207.14 |
| 6,877,512 B2 * | 4/2005 | Imai | A61M 16/0409 128/207.14 |
| 6,991,604 B2 * | 1/2006 | Cantrell | A61B 1/267 600/199 |
| 8,104,468 B2 * | 1/2012 | Chen | A61M 16/0409 128/206.16 |
| 8,464,710 B1 * | 6/2013 | Franckowiak | A61M 16/0488 128/207.14 |
| 8,715,171 B2 * | 5/2014 | Pastron | A61M 16/0495 600/187 |

(Continued)

*Primary Examiner* — Justine R Yu
*Assistant Examiner* — Matthew D Ziegler
(74) *Attorney, Agent, or Firm* — Distinct Patent Law; Justin P. Miller

(57) ABSTRACT

An oral and nasal tracheal intubation assistance device for assisting in endotracheal intubation includes an esophageal plug portion and a ramped guidance portion. The oral and nasal tracheal intubation assistance device temporarily occludes the esophageal inlet while providing a guided pathway for endotracheal tube placement into the trachea. The oral and nasal tracheal intubation assistance device includes a handle with an ergonomic grip oriented perpendicular to the body via a curved transition portion. Two primary embodiments are disclosed: an oral version for orotracheal intubation and a nasal version for nasotracheal intubation. The ramped guidance portion includes a capture segment and a guidance segment that work in concert to redirect and guide the endotracheal tube toward the tracheal inlet. The oral and nasal tracheal intubation assistance device provides a standardized approach to both oral and nasal intubation procedures while improving first-pass success rates.

16 Claims, 19 Drawing Sheets

(56)      References Cited

U.S. PATENT DOCUMENTS

| | | | | |
|---|---|---|---|---|
| 8,740,782 | B2 * | 6/2014 | McGrath | ................ A61B 1/267 |
| | | | | 600/196 |
| 9,795,753 | B2 * | 10/2017 | Qiu | ........................ A61B 1/267 |
| 10,245,093 | B2 | 4/2019 | Dunn | |
| 10,542,873 | B2 * | 1/2020 | Uesugi | ................... A61B 1/015 |
| 2008/0230056 | A1 | 9/2008 | Boedeker | |

* cited by examiner

100

110

116

151    152

118

ORAL AND NASAL TRACHEAL INTUBATION ASSISTANCE DEVICE

FIELD

The present invention relates generally to medical devices for assisting in endotracheal intubation procedures. More specifically, the invention relates to devices for guiding the placement of endotracheal tubes during both oral and nasal intubation procedures.

BACKGROUND

Endotracheal intubation is a critical medical procedure performed millions of times annually in operating rooms, emergency departments, and intensive care units worldwide. The procedure involves placing a breathing tube through either the mouth—orotracheal intubation—or nose—nasotracheal intubation—and into the trachea to establish a secure airway for mechanical ventilation. Success of this procedure is essential for patient survival in emergency situations and for airway management during surgical procedures.

Despite technological advances in video laryngoscopy, traditional direct laryngoscopy remains the primary method for endotracheal intubation. But this approach presents several challenges. For example, the practitioner must navigate complex throat anatomy, including the potential for the tube to enter the esophagus instead of the trachea. Failed first attempts at intubation can lead to tissue trauma, oxygen desaturation, and in severe cases, patient mortality.

The need exists for an oral and nasal tracheal intubation assistance device that can provide consistent, reliable guidance of endotracheal tubes into the trachea while preventing inadvertent esophageal intubation and injury to the cricoid cartilage, which is part of the anterior tracheal wall.

SUMMARY

The present invention addresses these needs by providing an oral and nasal tracheal intubation assistance device that temporarily occludes the esophageal inlet while simultaneously guiding an endotracheal tube into the trachea via a more anatomically correct pathway. The oral and nasal tracheal intubation assistance device includes an esophageal plug portion that sits at the upper esophageal sphincter and a ramped guidance portion that terminates at the supraglottis.

In one embodiment, the invention provides a nasotracheal intubation assistance device—N-TAD—configured for insertion of an endotracheal tube through a patient's nose. In another embodiment, the invention provides an orotracheal intubation assistance device—O-TAD—configured for insertion of an endotracheal tube through a patient's mouth. Both embodiments share core functional components while being adapted to their specific insertion pathways.

The ramped guidance portion includes a capture segment that initially engages the endotracheal tube, followed by a guidance segment that alters the direction of the endotracheal tube to pass into the trachea. Unlike conventional tube guides that fully encircle the endotracheal tube, the ramps include an open side extending along their entire length. This open-sided design allows the oral and nasal tracheal intubation assistance device to only partially surround the endotracheal tube during guided insertion, enabling lateral separation of the device from the tube after successful intubation. Specifically, the practitioner can readily withdraw the oral and nasal tracheal intubation assistance device by moving it sideways away from the secured endotracheal tube, eliminating the need to slide the device back over the full length of the tube, which improves the safety of airway securement.

Restated, the multipart ramp does not fully surround the endotracheal tube at any position—the device can be removed from the patient at any time without dislodging or passing over the endotracheal tube.

The oral and nasal tracheal intubation assistance device includes an ergonomically designed handle with a grip portion oriented perpendicular to a longitudinal axis of the body, the direction change accomplished via a curved transition portion. The handle attachment point is offset from the central axis of the ramp to prevent interference with endotracheal tube placement.

The handle is integrated with the proximal end of the body, and the plug is integrated with the distal end of the body.

With respect to the embodiment of the oral and nasal tracheal intubation assistance device intended for use for oral intubation, the device requires visualization via direct or indirect laryngoscopy. The oral embodiment is not intended for use in blind intubation.

Multiple size variations accommodate different patient anatomies, including pediatric models. The oral and nasal tracheal intubation assistance device is constructed of flexible, biocompatible materials and has demonstrated efficacy in both anatomical models and cadaver studies.

The flexible material is preferably a polymer with a shore hardness of approximately 80A. This hardness provides flexibility for anatomical conformity while maintaining structural integrity for endotracheal tube guidance. Anticipated methods of manufacturing include 3D printing and injection molding.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
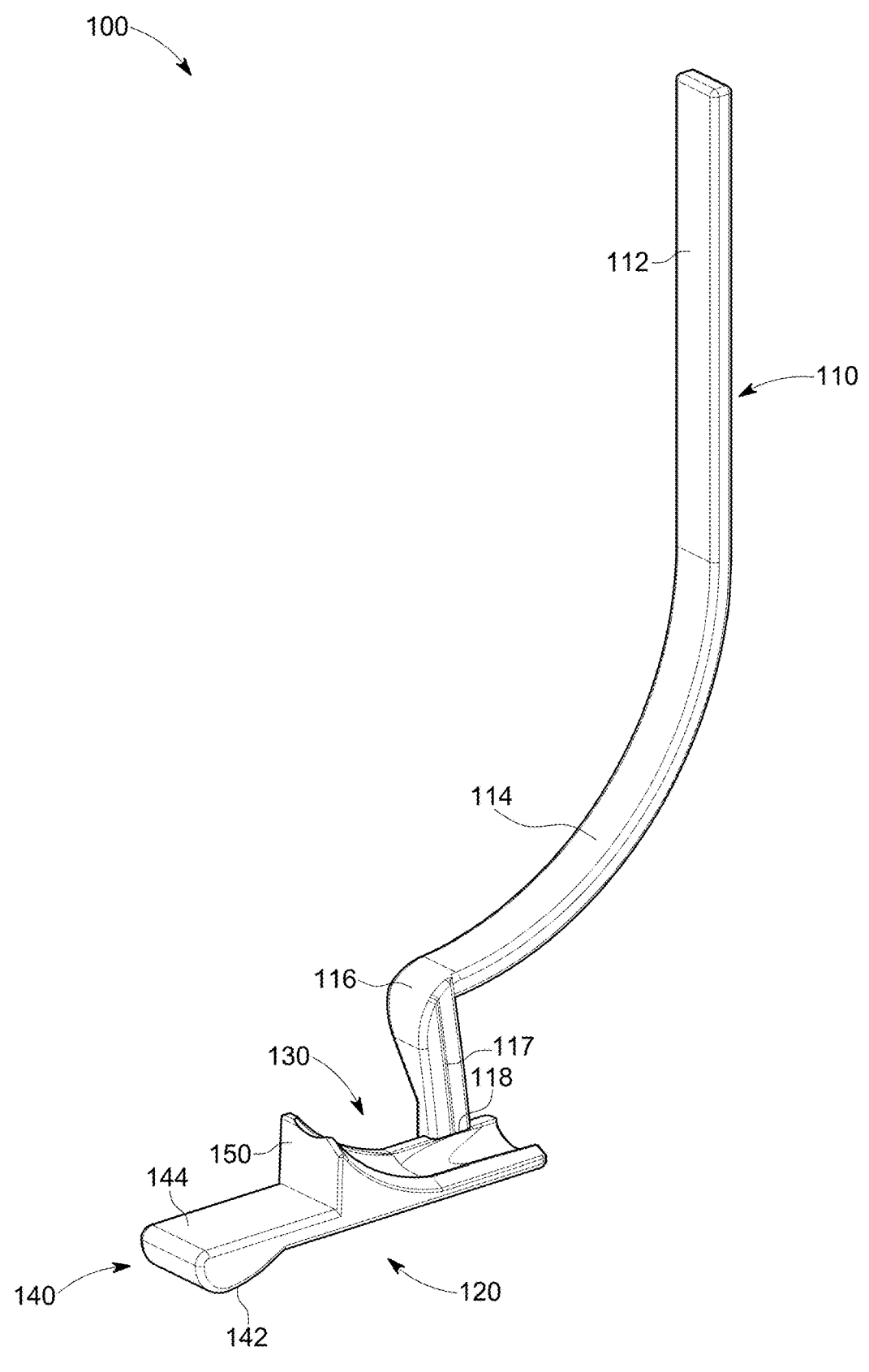
FIG. 1 illustrates a first isometric view of the first embodiment of the oral and nasal tracheal intubation assistance device.

Reference will now be made in detail to the presently preferred embodiments of the invention, examples of which are illustrated in the accompanying drawings. Throughout the following detailed description, the same reference numerals refer to the same elements in all figures.

Figure 2:
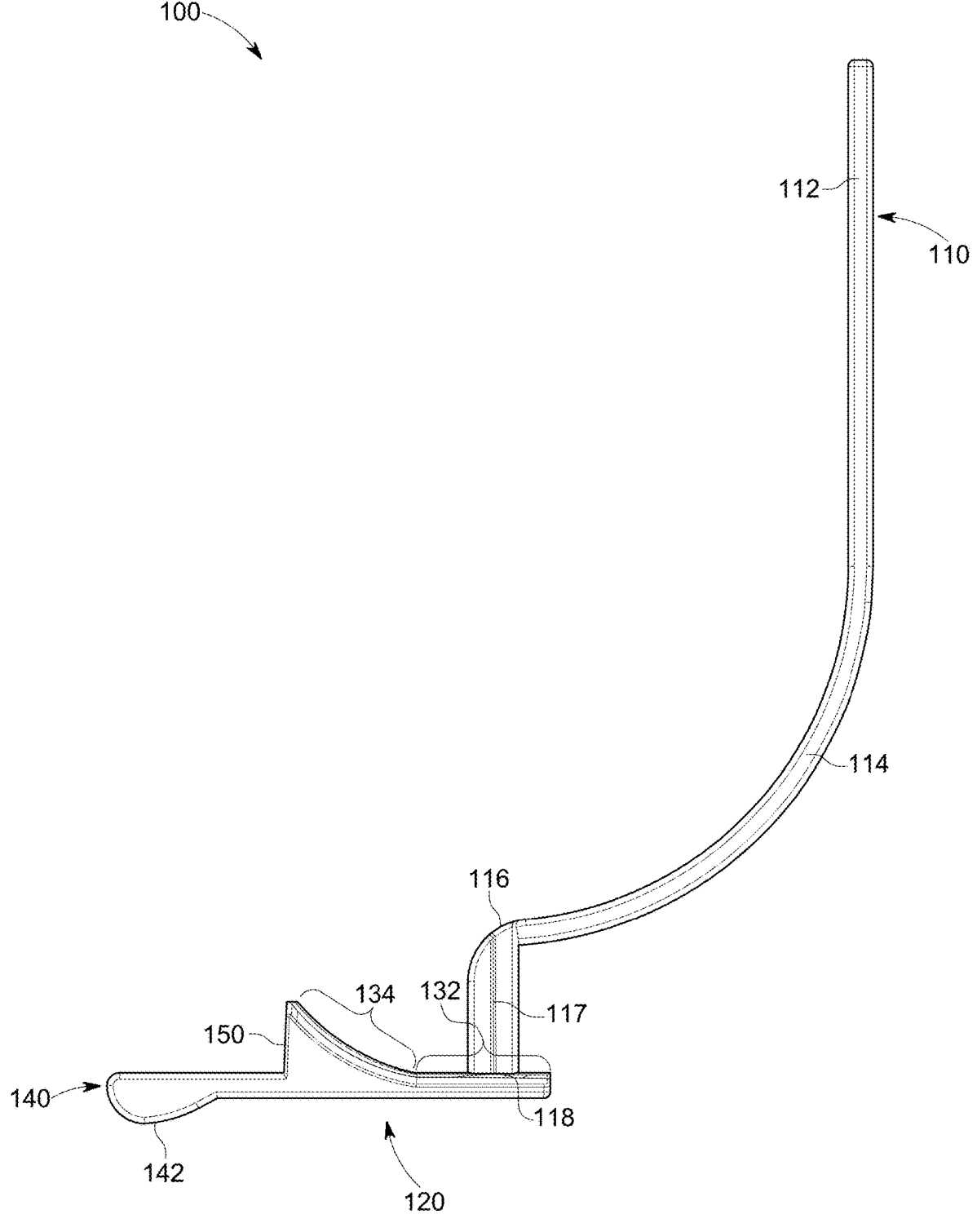
FIG. 2 illustrates a first side view of the first embodiment of the oral and nasal tracheal intubation assistance device.
Figure 3:
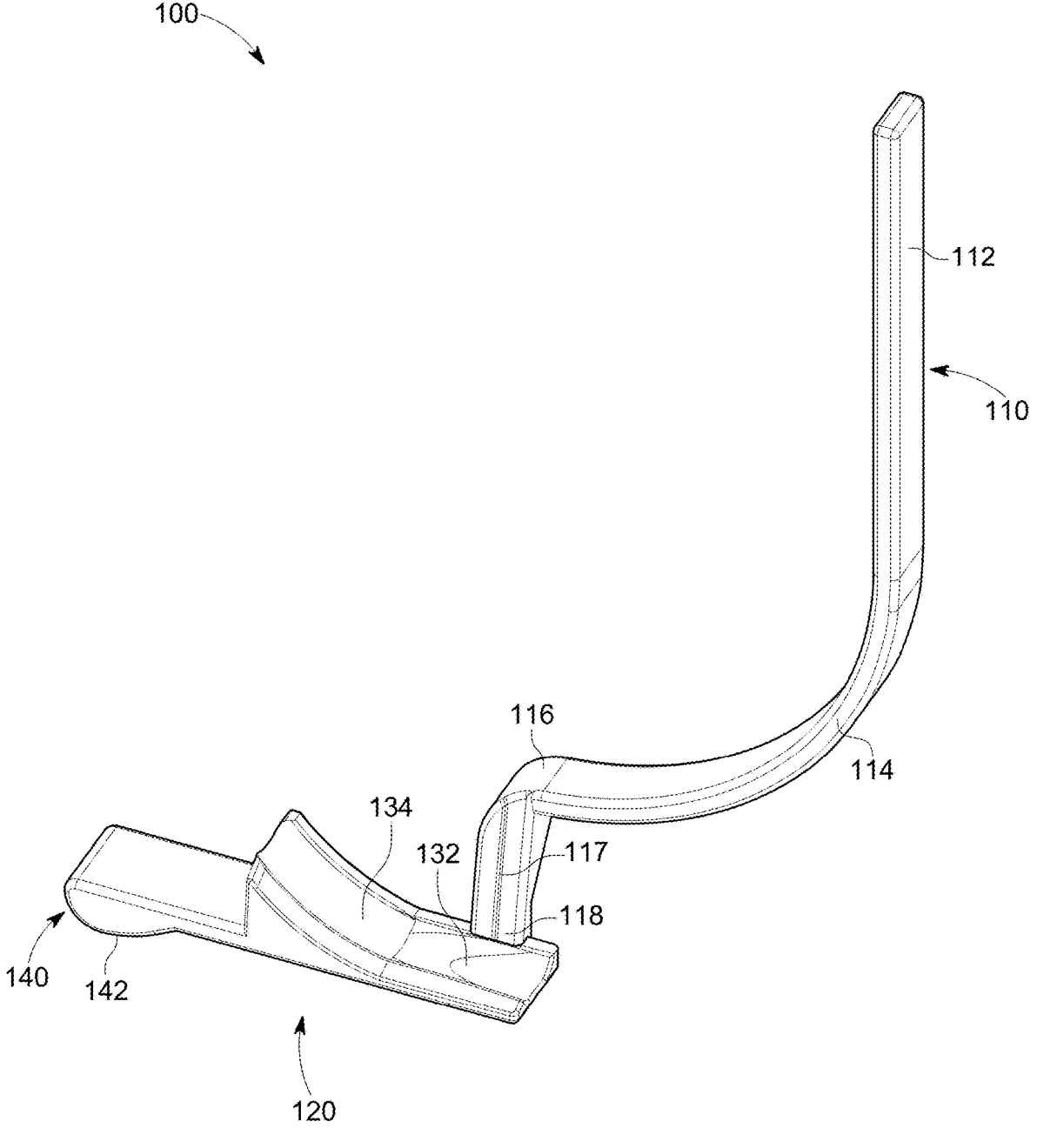
FIG. 3 illustrates a second isometric view of the first embodiment of the oral and nasal tracheal intubation assistance device.

Referring to FIGS. 1, 2, and 3, a first isometric view, a first side view, and a second isometric view of the first embodiment of the oral and nasal tracheal intubation assistance device are shown.

The oral and nasal tracheal intubation assistance device 100 is shown with an offset handle 110. This first embodiment of the oral and nasal tracheal intubation assistance device 100 is intended for use with insertion of the endotracheal tube 200 (see FIG. 6) through the nose. The offset handle 110 prevents interference between any portion of the offset handle 110 and the endotracheal tube 200 during insertion of the endotracheal tube 200.

The offset handle 110 includes a grip 112 for the doctor's hand, connected to a curved transition 114 that gradually accomplishes an approximate 90° shift in angle toward a plane parallel to the body 120. The handle continues via a connection to an angular transition 116 accomplishing an additional 90° shift in angle to the vertical transition 117 and finally to the offset attachment point 118.

The body 120 of the oral and nasal tracheal intubation assistance device 100 includes the multipart ramp 130 with capture segment 132, where the endotracheal tube 200 (see FIG. 6) first interacts with the multipart ramp 130, and the guidance segment 134, which alters the direction of the endotracheal tube 200 to pass into the trachea.

An end of the body includes the plug 140 that blocks passage of the endotracheal tube 200 into the esophagus. The plug 140 includes the plug protrusion 142, which acts to increase the height of the plug in the Z-direction to better fit the esophagus, without requiring a consistent increase in thickness of the entire body 120, which would make manipulation of the oral and nasal tracheal intubation assistance device 100 more difficult.

The plug upper face 144 is preferably flat, allowing for passage of the plug 140 into the hypopharynx at the junction of the supraglottis and hypopharynx, the insertion stop 150 resting against the arytenoids to prevent or limit insertion beyond the desired depth. The plug obstructs the esophageal inlet, the multipart ramp 130 guiding insertion of a breathing tube to the glottis and into the trachea.

Figure 4:
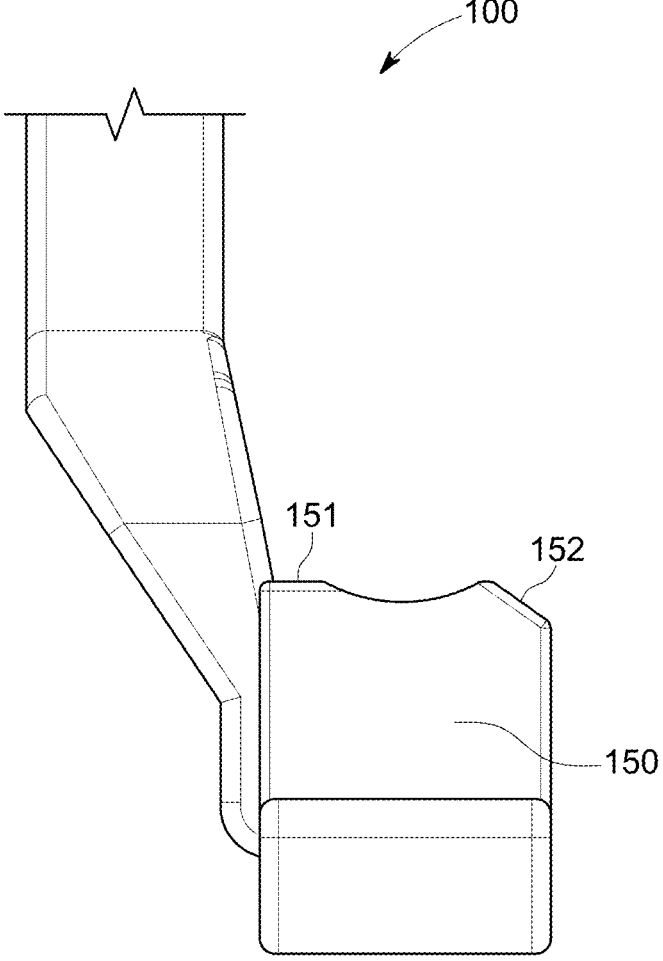
FIG. 4 illustrates a front view of the first embodiment of the oral and nasal tracheal intubation assistance device.

Referring to FIG. 4, a front view of the first embodiment of the oral and nasal tracheal intubation assistance device is shown.

The oral and nasal tracheal intubation assistance device 100 is shown with the insertion stop 150 including a clipped corner 152. As compared to the non-clipped corner 151, the clipped corner 152 of the insertion stop 150 eases insertion and removal of the oral and nasal tracheal intubation assistance device 100 where corners of the insertion stop 150 would catch on the patient's anatomy.

Figure 5:
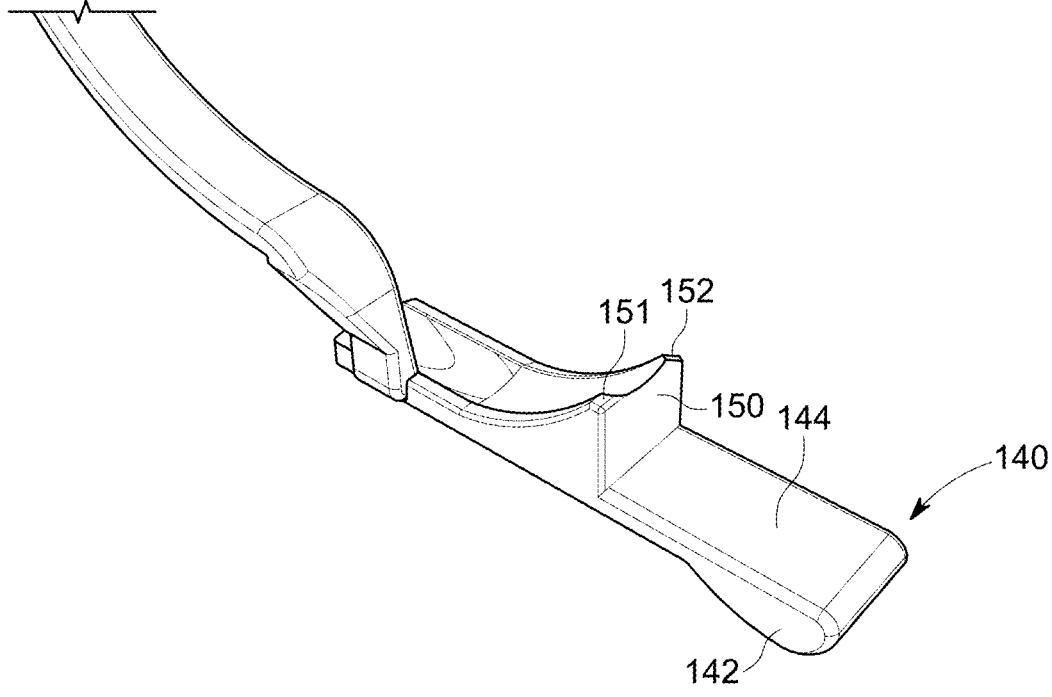
FIG. 5 illustrates a third isometric view of the first embodiment of the oral and nasal tracheal intubation assistance device.

Referring to FIG. 5, a third isometric view of the first embodiment of the oral and nasal tracheal intubation assistance device is shown.

The plug 140 is shown with plug protrusion 142 and plug upper face 144.

The insertion stop 150 is shown with non-clipped corner 151 and clipped corner 152.

Figure 6:
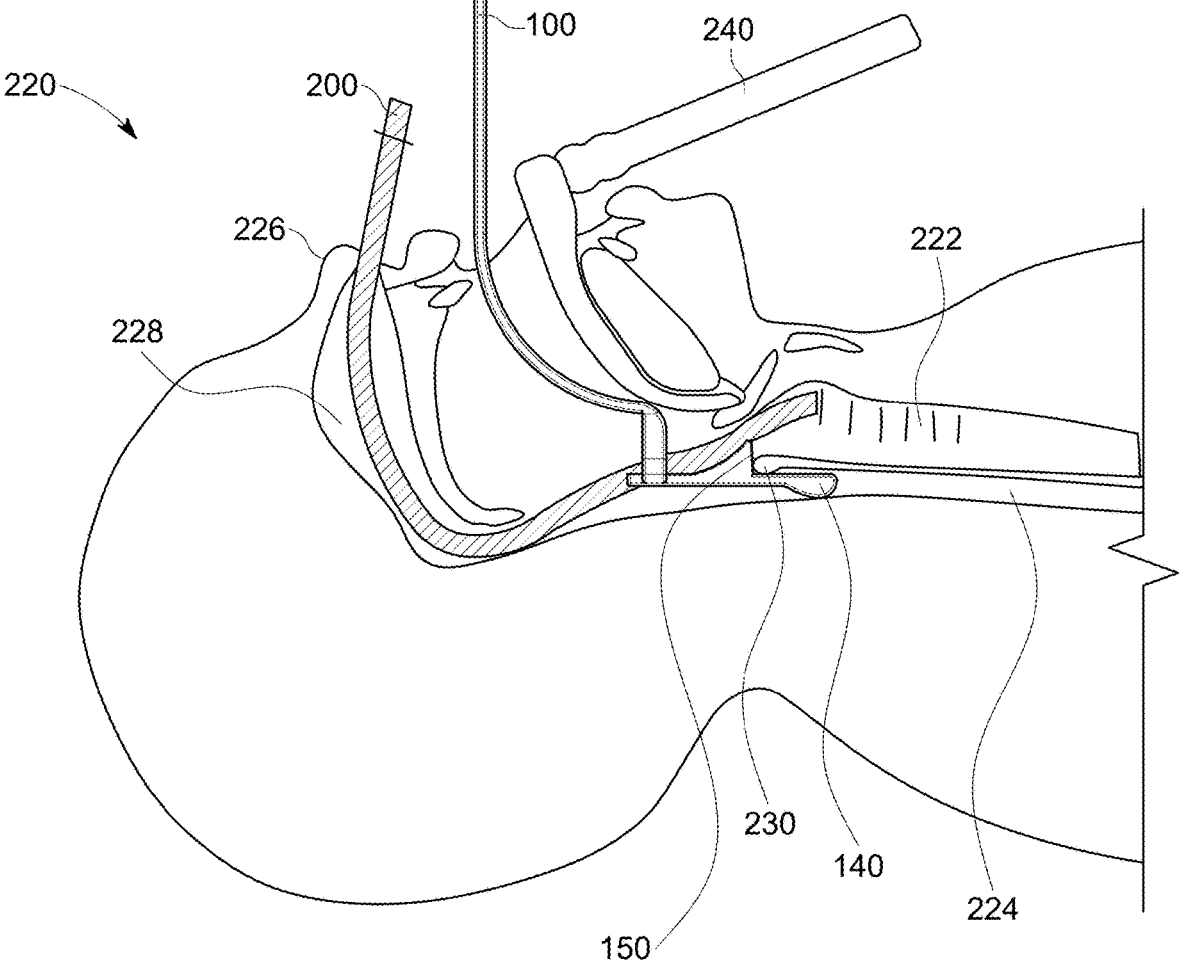
FIG. 6 illustrates a cross-sectional view of the first embodiment in use of the oral and nasal tracheal intubation assistance device.
Figure 7:
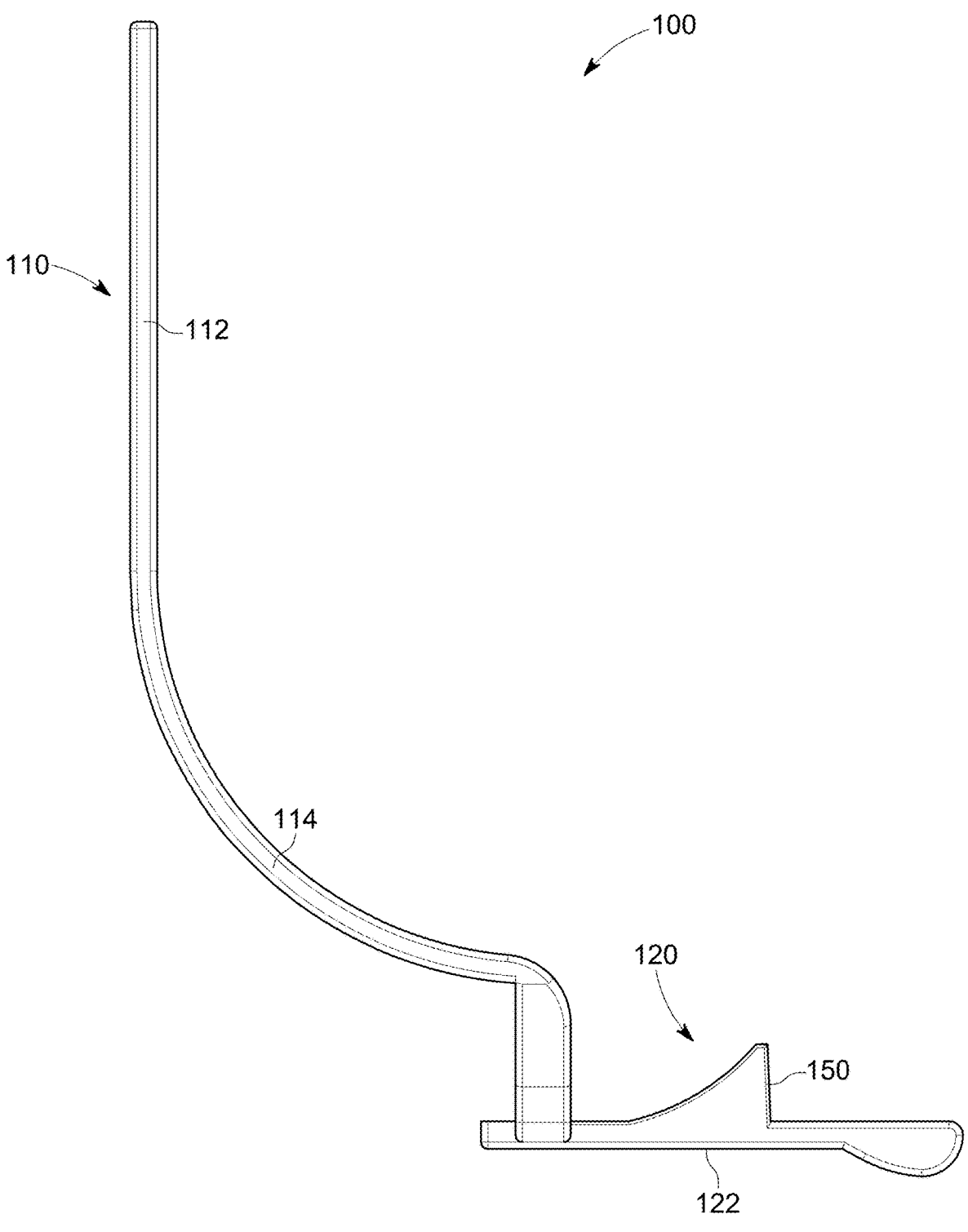
FIG. 7 illustrates a second side view of the first embodiment of the oral and nasal tracheal intubation assistance device.
Figure 8:
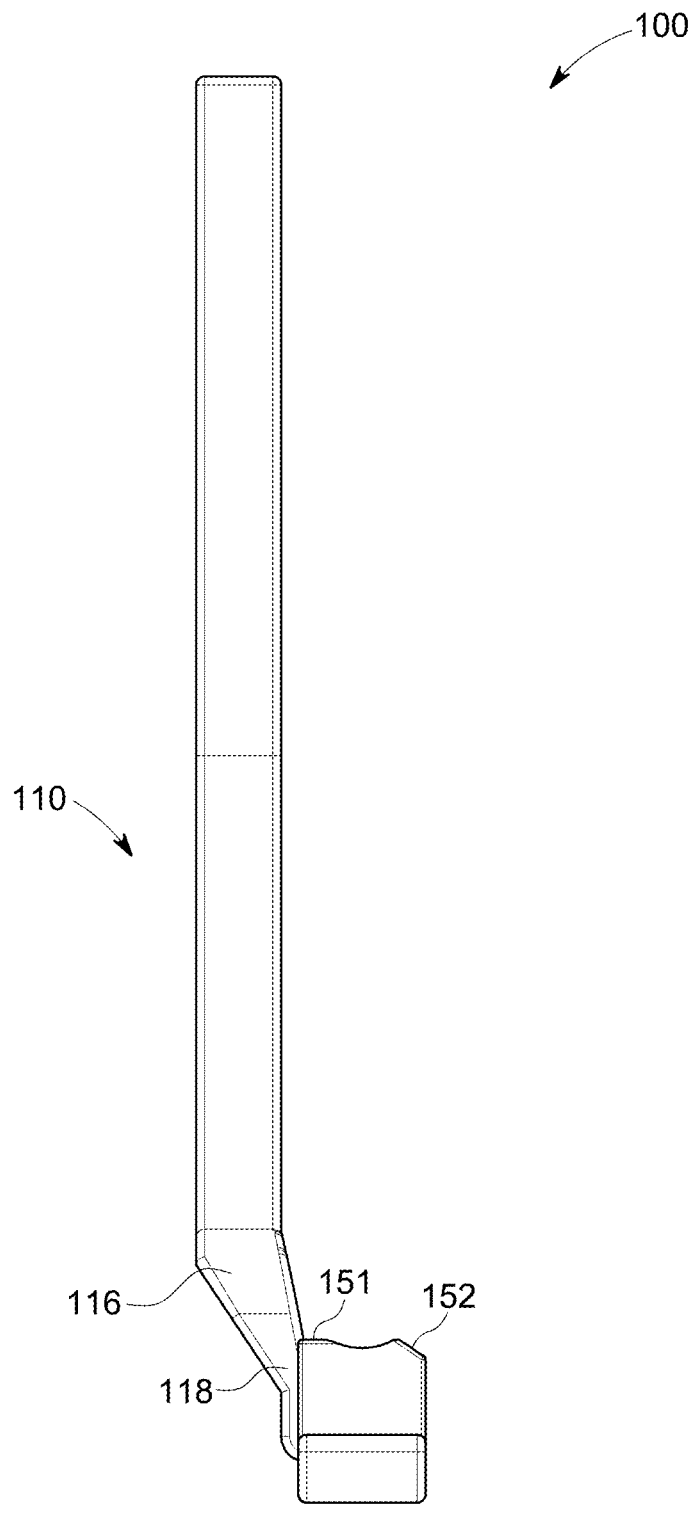
FIG. 8 illustrates a rear view of the first embodiment of the oral and nasal tracheal intubation assistance device.
Figure 9:
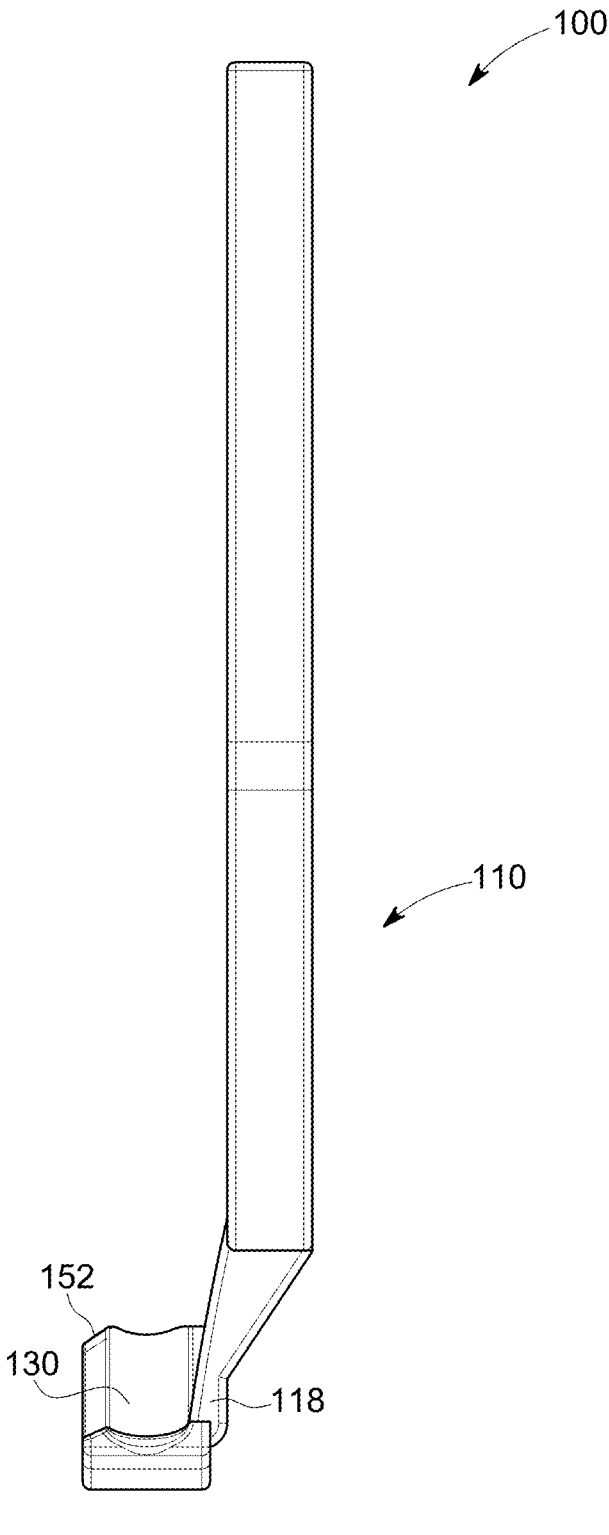
FIG. 9 illustrates a second front view of the first embodiment of the oral and nasal tracheal intubation assistance device.
Figure 10:
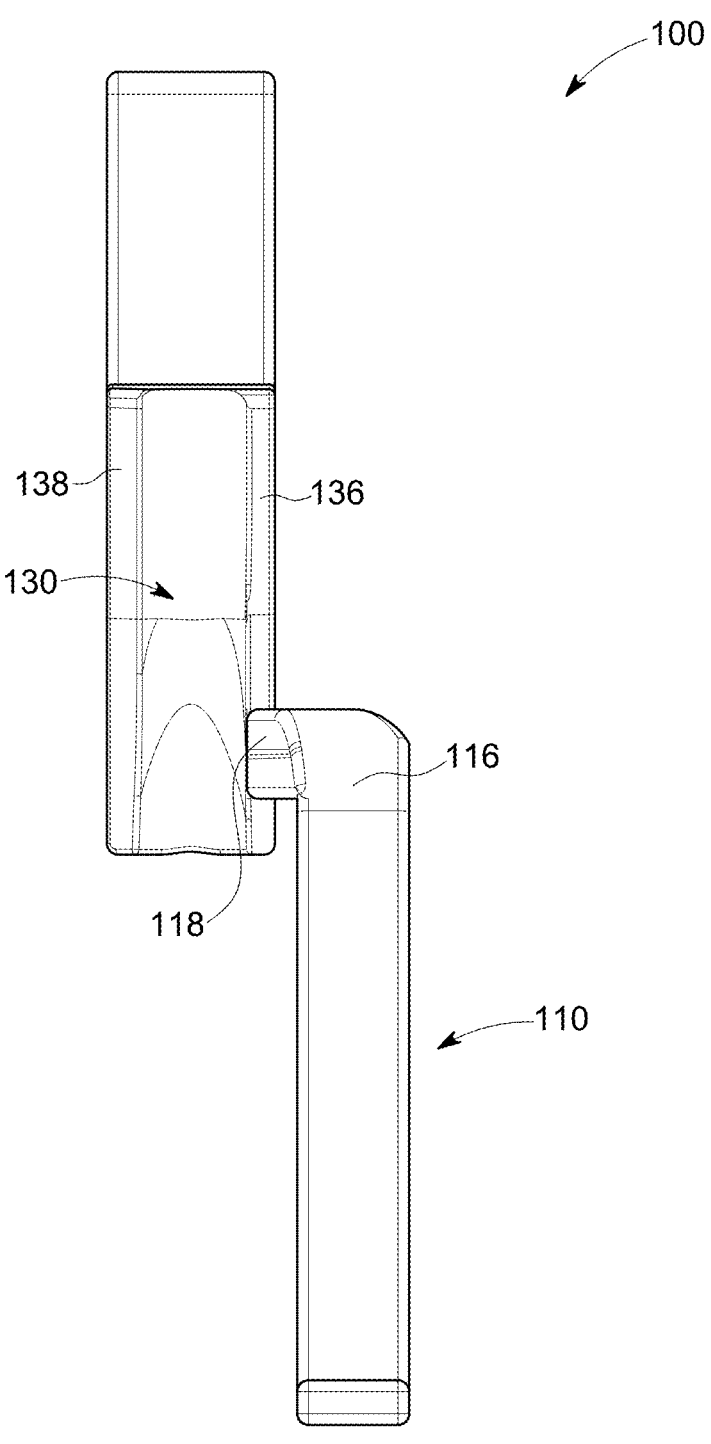
FIG. 10 illustrates a top view of the first embodiment of the oral and nasal tracheal intubation assistance device.
Figure 11:
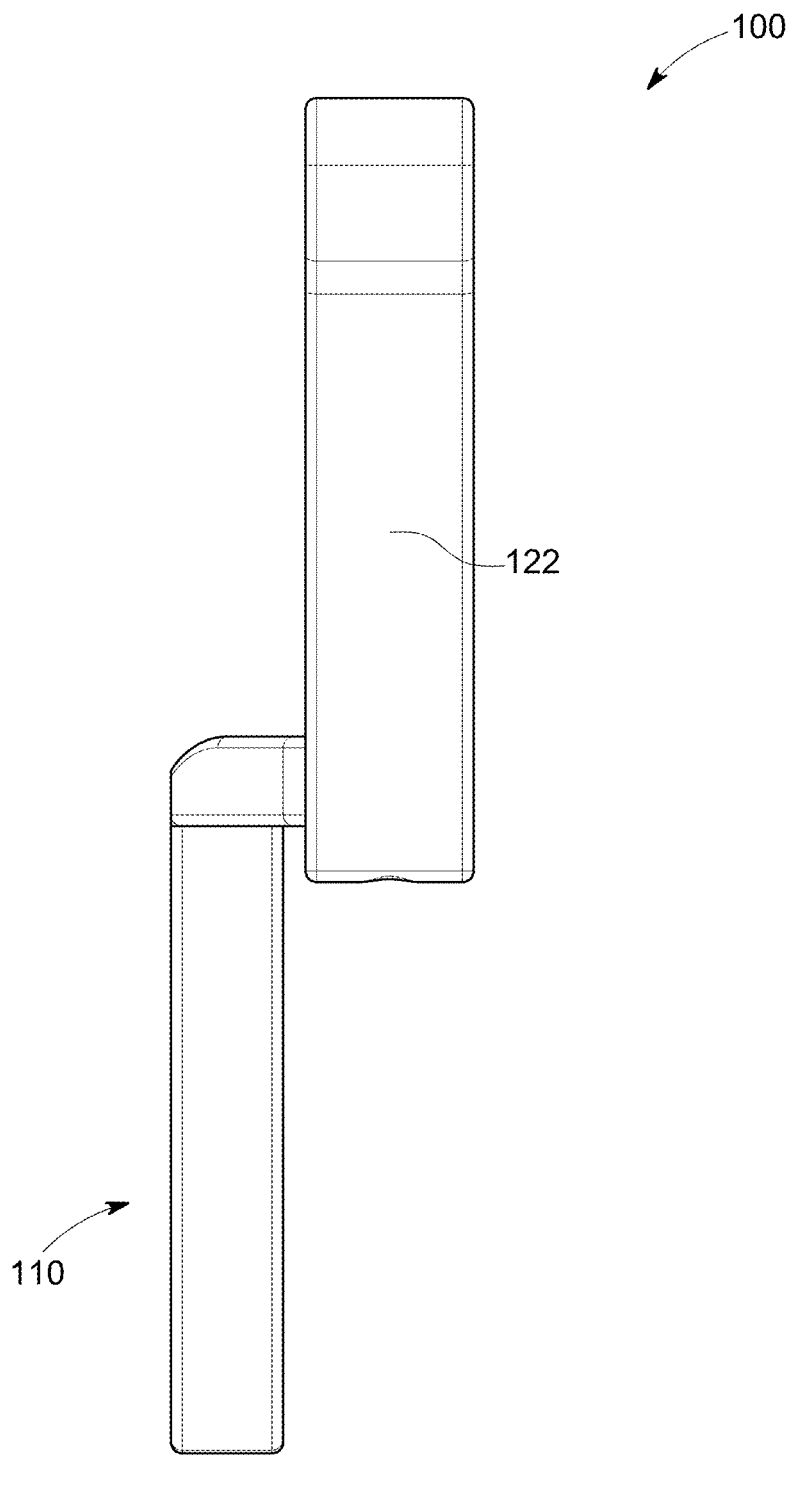
FIG. 11 illustrates a bottom view of the first embodiment of the oral and nasal tracheal intubation assistance device.
Figure 12:
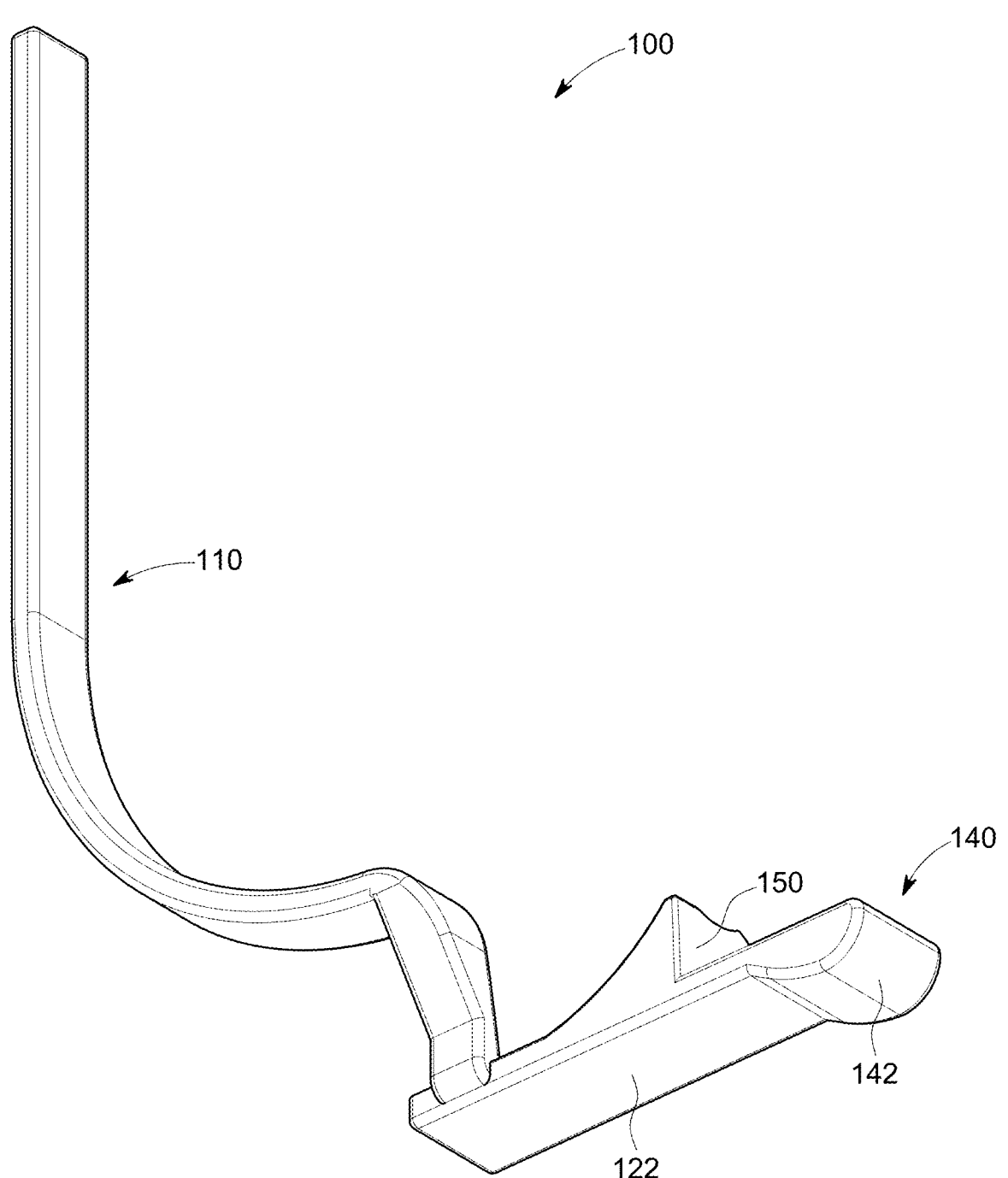
FIG. 12 illustrates a fourth isometric view of the first embodiment of the oral and nasal tracheal intubation assistance device.

Referring to FIG. 6, a cross-sectional view of the first embodiment in use of the oral and nasal tracheal intubation assistance device is shown.

The oral and nasal tracheal intubation assistance device 100 is shown being used with a patient 220. A laryngoscope 240 is used to open the airway in preparation for insertion of the endotracheal tube 200. The endotracheal tube 200 is passed through the nose 226, the nasal cavity 228, and then guided by the oral and nasal tracheal intubation assistance device 100. The insertion stop 150 rests against the arytenoid cartilages (supraglottis) 230, preventing over-insertion. The plug 140 rests within the hypopharynx 224, blocking the upper esophageal sphincter and ensuring that the endotracheal tube 200 is passed into the trachea 222.

Referring to FIGS. 7 through 12, multiple views of the first embodiment of the oral and nasal tracheal intubation assistance device are shown.

The offset handle 110 of the oral and nasal tracheal intubation assistance device 100 is visible in multiple figures. The offset handle 110, including the offset attachment point 118 and angular transition 116, ensures that the grip 112 is laterally offset from the multipart ramp 130. By having the offset handle 110 fully laterally offset from the multipart ramp 130, the endotracheal tube 200 (see FIG. 6) passes across the multipart ramp 130 without any interference with the offset handle 110 or its connection points.

The body includes body lower face 122, preferably shaped as a flat, planar surface. This surface is inset with respect to the plug 140, specifically the plug protrusion 142, easing insertion of the oral and nasal tracheal intubation assistance device 100 into the patient by providing additional clearance with respect to the patient's airway.

The insertion stop 150 with clipped corner 152 and non-clipped corner 151 is also visible. The clipped corner 152 reduces the interference points during insertion and removal of the oral and nasal tracheal intubation assistance device 100.

The multipart ramp 130 includes the curved, scooping, self-centering central section, assisting with guidance and automatic centering of the endotracheal tube 200 during insertion. Adjacent to the multipart ramp 130 are the first edge 136 and the second edge 138. Contact between the endotracheal tube 200 and either the first edge 136 or the second edge 138 helps to push the endotracheal tube 200 back toward the center of the multipart ramp 130, ensuring guidance during insertion.

Figure 13:
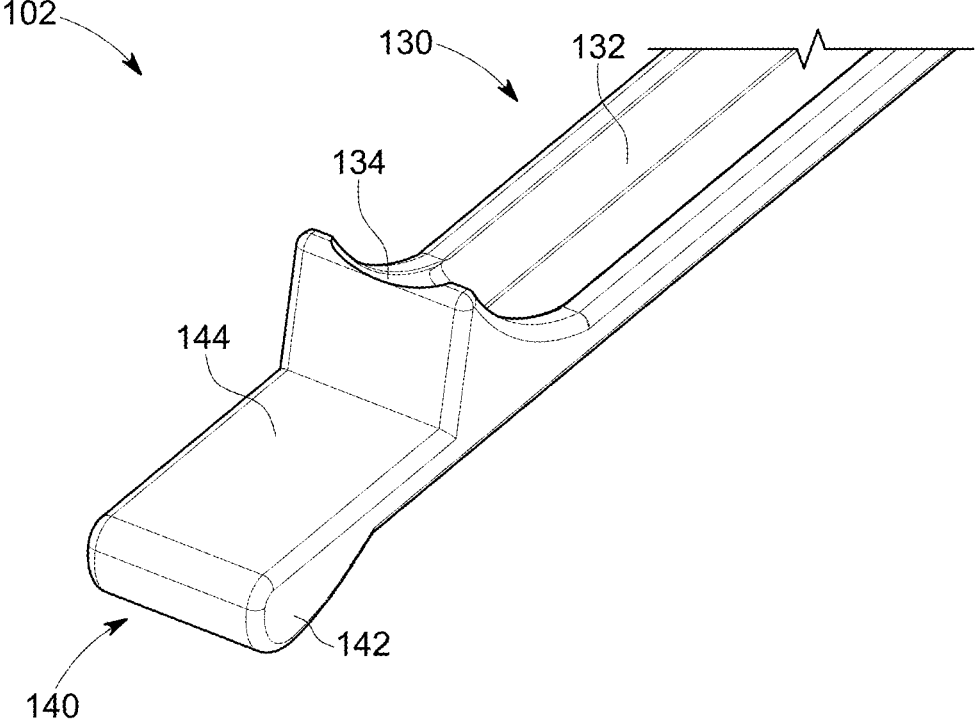
FIG. 13 illustrates a first isometric view of the second embodiment of the oral and nasal tracheal intubation assistance device.
Figure 14:
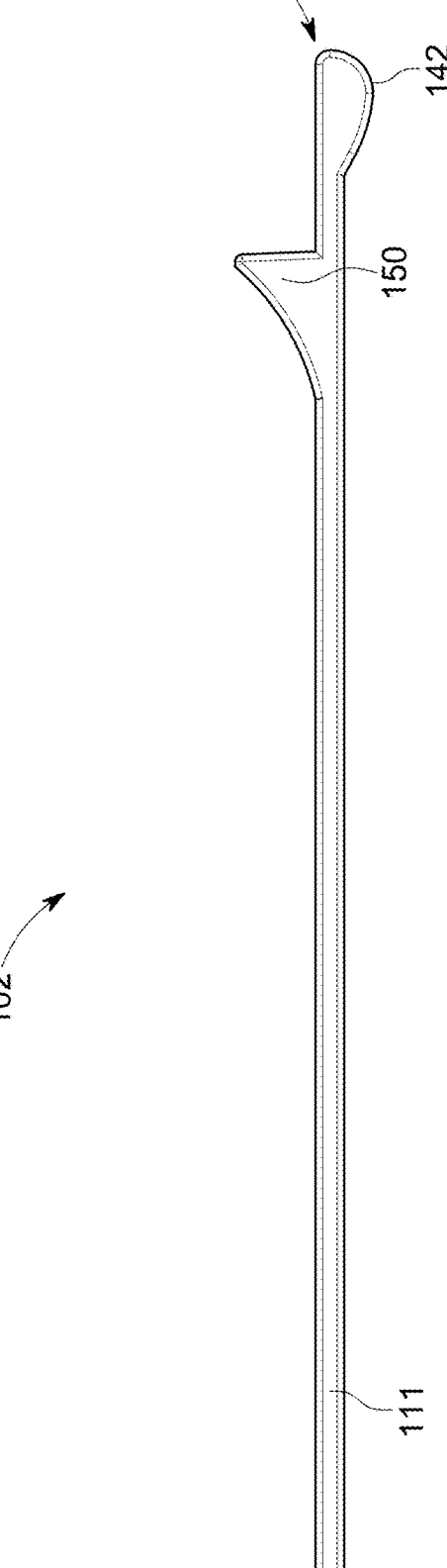
FIG. 14 illustrates a side view of the second embodiment of the oral and nasal tracheal intubation assistance device.
Figure 15:
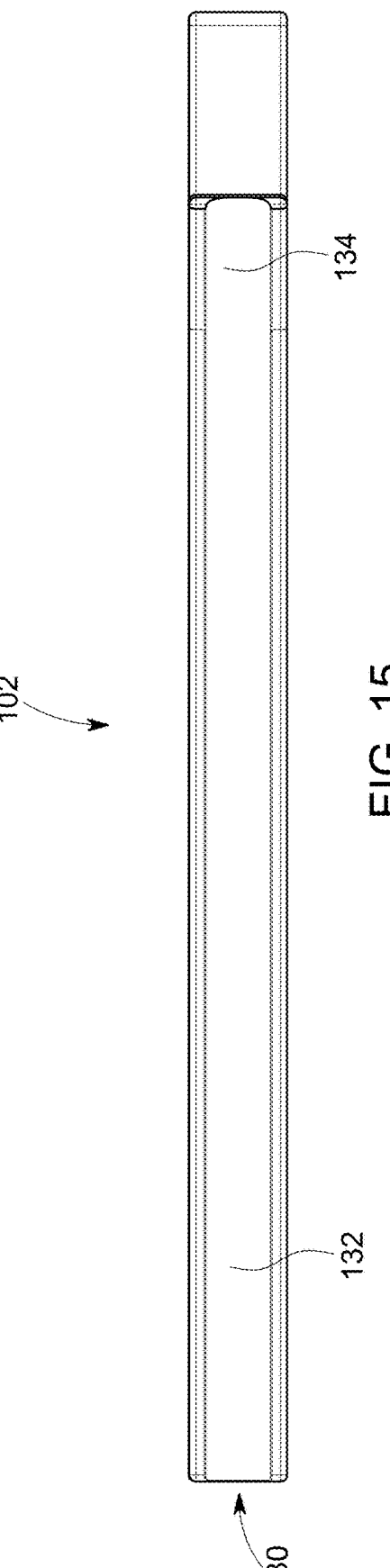
FIG. 15 illustrates a top view of the second embodiment of the oral and nasal tracheal intubation assistance device.
Figure 16:
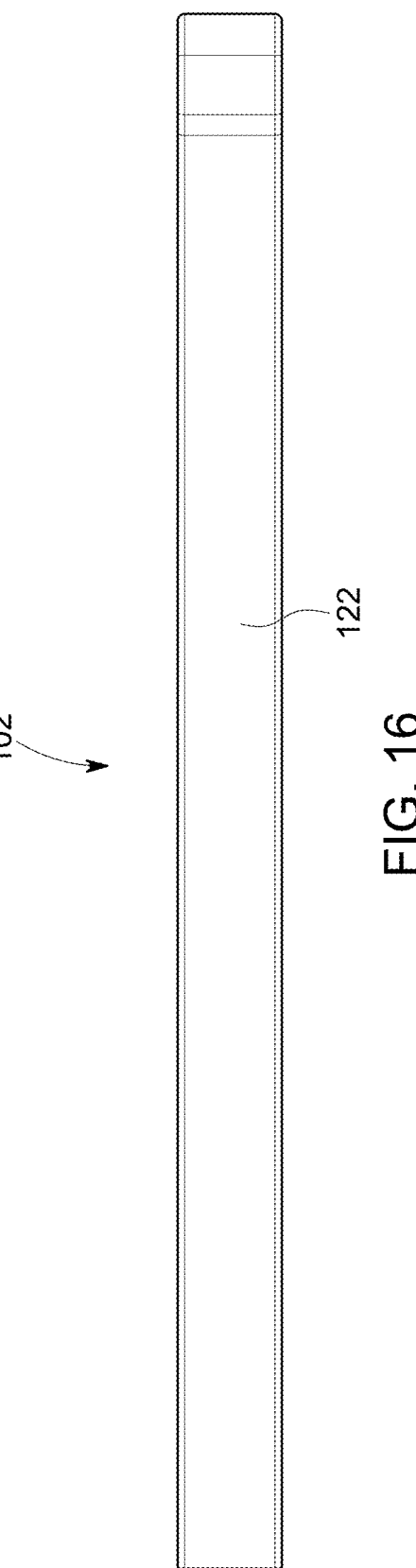
FIG. 16 illustrates a bottom view of the second embodiment of the oral and nasal tracheal intubation assistance device.
Figure 17:
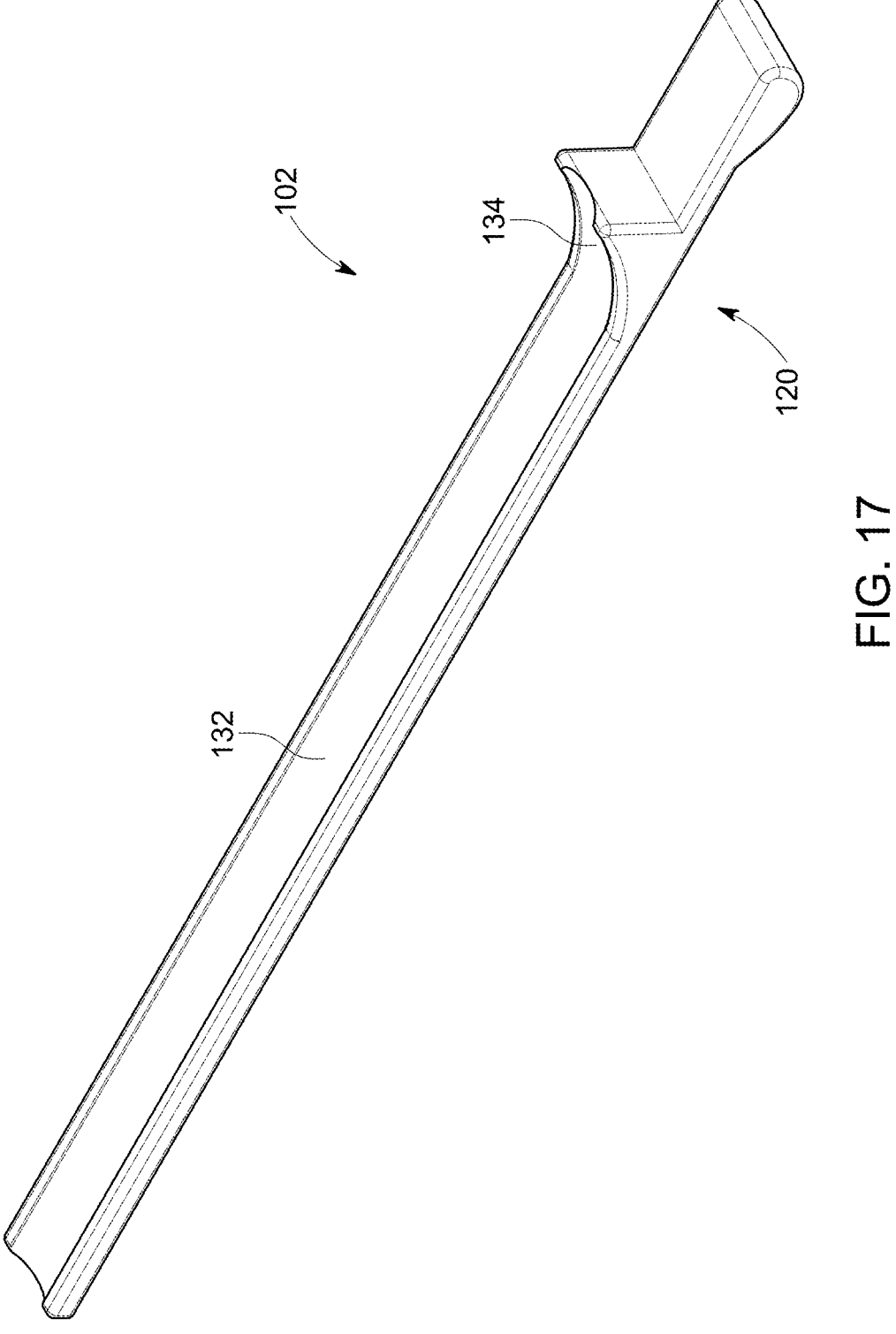
FIG. 17 illustrates an isometric view of the second embodiment of the oral and nasal tracheal intubation assistance device.
Figure 18:
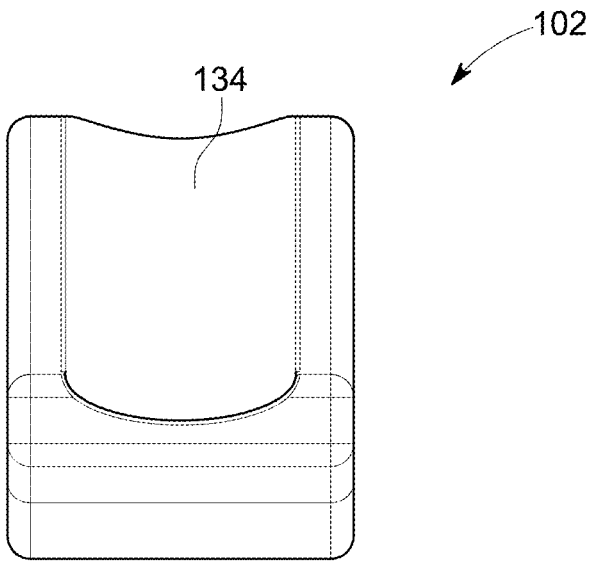
FIG. 18 illustrates a rear view of the second embodiment of the oral and nasal tracheal intubation assistance device.
Figure 19:
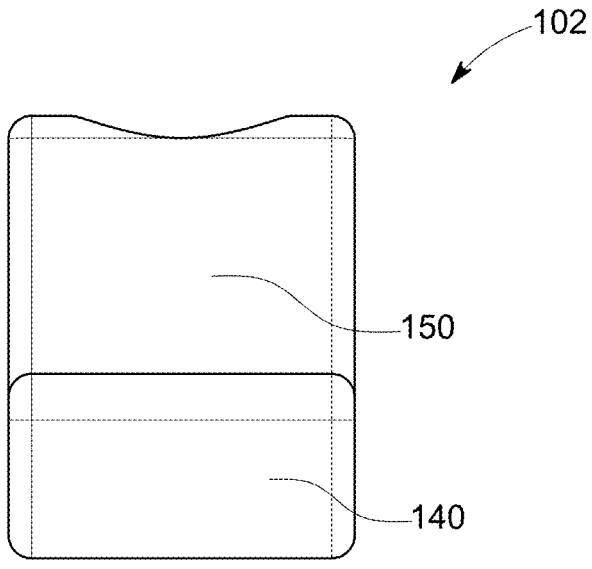
FIG. 19 illustrates a front view of the second embodiment of the oral and nasal tracheal intubation assistance device.

Referring to FIGS. 13 and 14, a first isometric view and a side view of the second embodiment of the oral and nasal tracheal intubation assistance device are shown.

The second embodiment of the oral and nasal tracheal intubation assistance device 102 is intended for use with oral intubation, rather than nasal intubation. The handle 111 is aligned with the body 120, and the multipart ramp 130 is integrated into the handle 111. The multipart ramp 130 again includes the capture segment 132 and guidance segment 134. By integrating the multipart ramp 130 with the handle 111, during use the endotracheal tube 200 passes along the multipart ramp 130 from the starting position outside of the patient, through the mouth, and ultimately into the trachea.

The handle 111 is formed from a flexible material, allowing it to bend during insertion of the oral and nasal tracheal intubation assistance device 102. The result is a gradual angular change in the multipart ramp 130, easing the process of guiding the endotracheal tube 200 (see FIG. 20) into the patient's trachea.

Referring to FIGS. 15 through 19, multiple views of the second embodiment of the oral and nasal tracheal intubation assistance device are shown.

The second embodiment of the oral and nasal tracheal intubation assistance device 102, intended for use in oral intubation, is shown with multipart ramp 130 including capture segment 132 and guidance segment 134. The handle 111 is combined with the capture segment 132 of the multipart ramp 130, controlling the path of the endotracheal tube 200.

The body 120 again includes body lower face 122 that is substantially plainer in its resting, flat position. Again, the handle 111 is formed from a flexible material and therefore the body lower face will curve as pressure is applied to the handle 111.

The multipart ramp 130 includes a curved inner surface to act to center the endotracheal tube during insertion.

The multipart ramp 130 is open, meaning that the multipart ramp 130 does not enclose the endotracheal tube 200 that is being guided into the patient. As a result, the second embodiment of the oral and nasal tracheal intubation assistance device 102 is readily removable from the patient.

The insertion stop 150 is again shown.

Figure 20:
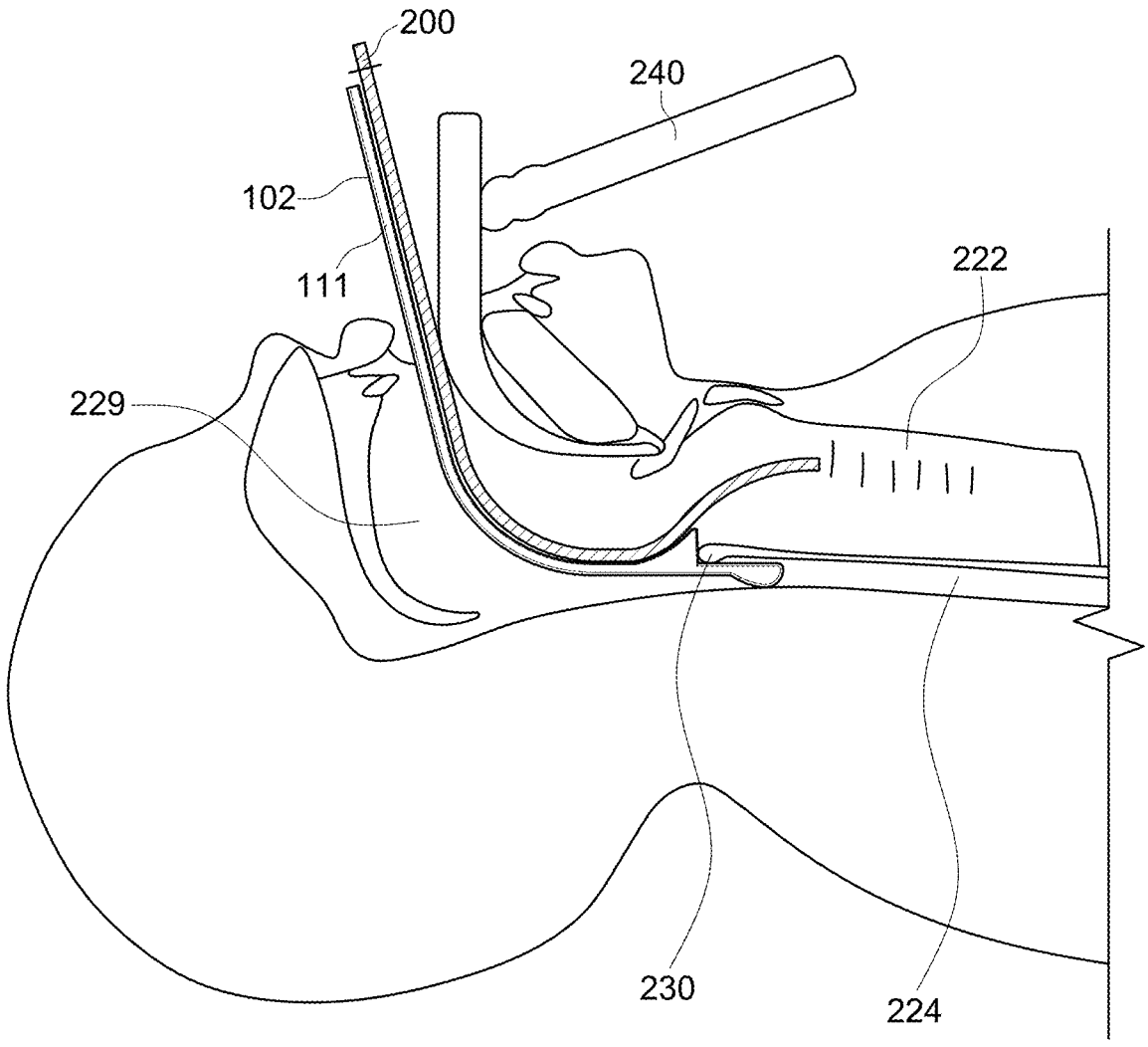
FIG. 20 illustrates a cross-sectional view of the second embodiment in use of the oral and nasal tracheal intubation assistance device.

Referring to FIG. 20, a cross-sectional view of the second embodiment in use of the oral and nasal tracheal intubation assistance device is shown.

The second embodiment of the oral and nasal tracheal intubation assistance device 102 is shown being used with a patient 220. A laryngoscope 240 is used to open the airway in preparation for insertion of the endotracheal tube 200. The endotracheal tube 200 is passed through the oral cavity 229, guided by the second embodiment of the oral and nasal tracheal intubation assistance device 102. The insertion stop 150 rests against the arytenoid cartilages (supraglottis) 230, preventing over-insertion. The plug 140 rests within the hypopharynx 224, ensuring that the endotracheal tube 200 is passed into the trachea 222.

The handle 111 of the second embodiment of the oral and nasal tracheal intubation assistance device 102 curves to guide the endotracheal tube 200 as it moves toward the trachea 222.

Equivalent elements can be substituted for the ones set forth above such that they perform in substantially the same manner in substantially the same way for achieving substantially the same result.

What is claimed is:

1. A nasotracheal intubation assistance device for guiding insertion of an endotracheal tube into a patient's trachea, comprising:

a body with a proximal end and a distal end;

the body including a multipart ramp, the multipart ramp comprising a capture segment and a guidance segment, wherein the multipart ramp is configured to only partially surround the endotracheal tube;

the body including a body lower face with a flat surface;

the capture segment at the proximal end of the body where the endotracheal tube initially engages the device, the capture segment parallel to the body lower face;

the guidance segment curved away from the body and configured to direct the endotracheal tube toward the patient's trachea; and a plug connected to the body;

the plug at the distal end of the body;

the plug configured to position at an upper esophageal sphincter and obstruct outflow of stomach contents;

a fixed offset handle connected to the body at an offset attachment point, the offset attachment point between the proximal end of the body and the distal end of the body, the offset attachment point positioned laterally to one side of the multipart ramp to prevent interference of the multipart ramp with the endotracheal tube during removal of the multipart ramp after endotracheal tube placement;

wherein the multipart ramp further comprises a first edge and a second edge defining an open side extending along a full length of the multipart ramp, the open side allowing lateral removal of the nasotracheal intubation assistance device from a position in contact with the endotracheal tube to a position separated from the endotracheal tube.

2. The nasotracheal intubation assistance device of claim 1, wherein the plug further comprises a plug protrusion and a plug upper face;

the plug upper face having a flat, planar surface that is parallel to the body lower face;

the plug protrusion extending past the body lower face; and the plug protrusion extending outward, away from the flat, planar surface of the plug upper face.

3. The nasotracheal intubation assistance device of claim 2, further comprising:

an insertion stop configured to limit insertion depth by being configured to rest against arytenoids to prevent or limit insertion beyond a desired depth;

the insertion stop perpendicular to the plug upper face and perpendicular to the body lower face.

4. The nasotracheal intubation assistance device of claim 3, wherein the insertion stop comprises a non-clipped corner and a clipped corner.

5. The nasotracheal intubation assistance device of claim 1, wherein the fixed offset handle comprises:

a grip;

a curved transition; and a vertical transition connecting the curved transition to the offset attachment point.

6. The nasotracheal intubation assistance device of claim 5, wherein the grip extends substantially perpendicular to a longitudinal axis of the body.

7. A tracheal intubation assistance device for guiding insertion of an endotracheal tube into a patient's trachea via a nasal passage, comprising:
 a body comprising a body lower face, a proximal end and a distal end;
  the body lower face having a planar surface;
 a plug connected to the body at the distal end, the plug configured to rest at an upper esophageal sphincter and obstruct outflow of stomach contents;
  the plug including a plug upper face, the plug upper face shaped to create a seal against the upper esophageal sphincter;
  the plug extending past the body lower face;
 a multipart ramp connected to the body, the multipart ramp comprising:
  a capture segment at the proximal end configured to initially engage the endotracheal tube;
  a guidance segment configured to alter a direction of the endotracheal tube to pass into the patient's trachea while contacting less than half of a circumference of the endotracheal tube; and
  a first edge and a second edge defining an open side extending along a length of the multipart ramp, the open side enabling lateral removal of the device from the endotracheal tube;
 an offset handle comprising:
  a grip extending perpendicular to the planar surface of the body lower face of the body;
  a curved transition connected to the grip; and
  a vertical transition connecting the curved transition to an offset attachment point positioned laterally to one side of the multipart ramp to prevent interference with the endotracheal tube during insertion;
  the offset attachment point connected to the body at a midpoint between the proximal end and the distal end;
 wherein the multipart ramp is configured to support the endotracheal tube from an underside thereof without enclosing the endotracheal tube, enabling lateral removal of the device from the endotracheal tube after endotracheal tube placement.

8. The tracheal intubation assistance device for guiding insertion of an endotracheal tube into a patient's trachea of claim 7, further comprising:
 an insertion stop configured to limit insertion depth by being configured to rest against arytenoids to prevent or limit insertion beyond a desired depth;
 the insertion stop perpendicular to the plug upper face.

9. The tracheal intubation assistance device for guiding insertion of an endotracheal tube into a patient's trachea of claim 7, wherein the device is sized for orotracheal intubation and configured for insertion through an oral cavity.

10. The tracheal intubation assistance device for guiding insertion of an endotracheal tube into a patient's trachea of claim 7, wherein the body is sized for nasotracheal intubation and configured for insertion through an oral cavity.

11. A tracheal intubation assistance device for guiding insertion of an endotracheal tube through a nasal passage and into a patient's trachea, comprising:
 a body having a proximal end and a distal end;
  the body including a body lower face with a planar surface;
 a handle integrated with the body and formed from a flexible material allowing the handle to bend during insertion;
  the handle meeting the body at a midpoint between the proximal end and the distal end;
 a multipart ramp integrated into the handle and the body, the multipart ramp comprising:
  a capture segment at the proximal end of the body, the capture segment configured to initially engage the endotracheal tube; and
  a guidance segment configured to alter a direction of the endotracheal tube to pass into the patient's trachea while maintaining contact with only a lower surface of the endotracheal tube;
 wherein the multipart ramp includes a first edge and a second edge defining an open side extending along a length of the multipart ramp, the open side facilitating device removal without tube displacement; and
 a plug at the distal end of the body configured to rest at an upper esophageal sphincter;
  the plug including a plug upper face;
  the plug upper face parallel to the body lower face;
  the plug extending past the body lower face.

12. The tracheal intubation assistance device of claim 11, wherein the multipart ramp comprises a curved inner surface configured to center the endotracheal tube during insertion.

13. The tracheal intubation assistance device of claim 11, further comprising:
 an insertion stop configured to limit insertion depth of the device by resting against a patient's arytenoids;
 the insertion stop perpendicular to a plug upper face and to the body lower face.

14. The tracheal intubation assistance device of claim 13, wherein the insertion stop comprises at least one clipped corner to reduce interference points during insertion and removal.

15. The tracheal intubation assistance device of claim 11, wherein the plug further comprises:
 a plug protrusion extending from the body; and
 a plug upper face configured to obstruct an upper esophageal inlet.

16. The tracheal intubation assistance device of claim 11, wherein the guidance segment is curved away from the body and configured to direct the endotracheal tube toward the patient's trachea.

* * * * *